United States Patent [19]

Amick

[11] Patent Number: 4,656,057

[45] Date of Patent: Apr. 7, 1987

[54] MICROBIOCIDAL ARTICLE FOR AQUEOUS SYSTEMS

[75] Inventor: David R. Amick, Chalfont, Pa.

[73] Assignee: Rohm and Haas Company, Philadelphia, Pa.

[21] Appl. No.: 755,768

[22] Filed: Jul. 17, 1985

Related U.S. Application Data

[60] Division of Ser. No. 518,237, Jul. 28, 1983, Pat. No. 4,552,752, which is a continuation-in-part of Ser. No. 462,242, Jan. 31, 1983, abandoned, which is a continuation-in-part of Ser. No. 422,056, Sep. 23, 1982, abandoned.

[51] Int. Cl.$^4$ .............................................. B05D 5/00
[52] U.S. Cl. .................................... 427/245; 424/406
[58] Field of Search ........................... 427/245; 424/15

[56] References Cited

U.S. PATENT DOCUMENTS

| | | | |
|---|---|---|---|
| 2,809,900 | 10/1957 | Sarbach | 427/245 |
| 3,055,297 | 9/1962 | Leeds | 427/245 |
| 3,639,306 | 2/1972 | Sternberg et al. | 427/245 |
| 4,432,875 | 2/1984 | Wrasidlo et al. | 427/245 |
| 4,505,889 | 3/1985 | Amick | 424/21 |
| 4,510,186 | 4/1985 | Kuriyama et al. | 427/245 |
| 4,552,752 | 11/1985 | Amick | 424/21 |

FOREIGN PATENT DOCUMENTS 1104926  7/1981  Canada .................................. 424/15

*Primary Examiner*—Ronald W. Griffin
*Attorney, Agent, or Firm*—Terence P. Strobaugh

[57] ABSTRACT

An improved article of a membrane permeable to water and impermeable to microbiocidal compounds containing therein a solid particulate microbiocidal composition which is useful in aqueous systems, wherein the composition is produced from aqueous solutions of a water-soluble microbiocidal compound absorbed in an inert, finely-divided water-insoluble solid carrier. Especially useful are microbiocidal 3-isothiazolones and 2-substituted-1,2-benzisothiazolones, and metal salt stabilized derivatives thereof, absorbed into a silicaceous diatomaceous earth in a sealed, perforated membrane, for example, a perforated bag, produced from polyethylene. These articles afford a form, which is safer for handling.

9 Claims, No Drawings

MICROBIOCIDAL ARTICLE FOR AQUEOUS SYSTEMS

This is a division of application Ser. No. 518,237 filed July 28, 1983, now U.S. Pat. No. 4,552,752, issued Nov. 12, 1985 which is a continuation-in-part of U.S. Ser. No. 462,242, filed Jan. 31, 1983, now abandoned, which is a continuation-in-part of Ser. No. 422,056 filed Sept. 23, 1982, now abandoned.

This invention relates to microbiocidal articles which are prepared from membranes permeable to external water and impermeable to microbiocidal compounds containing sealed therein particulate solid compositions of aqueous solutions of water-soluble microbiocidal compounds absorbed in an inert, finely-divided water-insoluble carrier material. Especially preferred are the microbiocidal 3-isothiazolones and 2-substituted-1,2-benzisothiazolones (hereafter "isothiazolones"). The isothiazolones have a tendency to effect skin irritancy in man and to evolve nontoxic gases when in aqueous solution at concentrations convenient for shipping. The invention also relates to a method of controlling living microorganisms using the microbiocidal articles, and to a method for safening the use of water soluble biocides.

Isothiazolones are a class of chemical compounds known to possess excellent and useful microbiocidal properties and resistance to common additives and contaminants. Many 3-isothiazolones are disclosed in U.S. Pat. Nos. 3,761,488; 3,849,430; 3,870,795; 4,067,878; 4,150,026; and 4,241,214. U.S. Pat. Nos. 3,517,022, 3,065,123; and 3,761,489 disclose 2-substituted-1,2-benzisothiazolones. U.S. Pat. No. 3,849,430 discloses a method for preparing the isothiazolones.

While the aforementioned patents disclose the use of isothiazolones in a variety of microbiocidal end uses, such as, for example, those uses and formulations and compositions disclosed in U.S. Pat. No. 3,761,488 at columns 15-19 and in the actual examples thereafter, isothiazolones are generally made available in combination with a liquid carrier such as water or in aqueous compositions. Column 19, line 66 et seq. discloses that isothiazolones can be taken up or mixed with a finely-divided particled solid carrier, as for example, clays, inorganic silicates, carbonates, silicas and organic carriers. Column 20, line 25 et seq. discloses that a convenient method for preparing a solid formulation is to impregnate the isothiazolone onto the solid carrier by means of a volatile solvent, such as acetone. However, earlier attempts to produce solid formulations have resulted in formulations which tended to coalesce (or "cake") or to give extremely lightweight particles (or "dusts").

U.S. Pat. No. 3,977,404 discloses an osmotic device for delivering an active agent to an external fluid present in the environment of use at a controlled and continuous rate comprised of a shaped wall, which is made in at least a part of a material permeable to an external fluid and substantially impermeable to active agents, surrounding at least part of a reservoir containing an active agent. The reservoir is formed of a microporous material permeable to the active agent and the external fluid. The micropores in the reservoir constitute a passageway for dispensing active agent from the reservoir to the external fluid in the environment of use wherein the external fluid is continuously imbibed through the wall into the reservoir in a tendency towards osmotic equilibrium at a rate determined by the permeability of the wall and the osmotic pressure gradient across the wall to continuously dissolve active agent to provide a substantially saturated solution of active agent which is delivered through the passageway from the device. The material for fabricating the wall is selected from materials which can be substantially insoluble in fluids or which can bioerode after a period of time taking place at the end of the active agent release period. Exemplary suitable wall materials include cellulose acetate and similar cellulose esters and cellulose ethers, hydroxylated ethylene-vinyl acetate; perm-selective aromatic nitrogen containing polymeric membranes that exhibit water permeability and essentially no solute permeability, semi-permeable membranes made from polymeric oxides; and the like. Suitable microporous material to produce the reservoir include polymeric materials such as polycarbonates, poly(vinyl chloride), polyamides, polysulfones, crosslinked olefin polymers, and hydrophobic or hydrophilic microporous homo-, co- and interpolymers. The examples teach only reservoirs produced from polymeric materials. Exemplary active agents include, for example, pesticides, herbicides, germicides, biocides, algicides, insecticides, antioxidants, plant growth promoters and inhibitors, disinfectants, catalysts, chemical reactants, nutrients, cosmetics, drugs, sex sterilants, air purifiers, and other agents which benefit the environment of use.

The devices of the patent are made by standard techniques. For example, one suitable technique is to form the reservoir by blending a polymeric powder with an active agent in crystalline or granular form and then applying pressure to convert the blend into a solid having agent embedded therein followed by applying the wall by spraying, dipping, casting, coating, solvent evaporation, molding, or pressing the wall-forming material to the reservoir. The opening in the wall can be formed by covering a part of the wall with tape that is removed after the wall is coated onto the reservoir, by cutting away a part of the wall, or by punching an opening in the wall to connect a microporous path of the reservoir with the exterior of the device.

U.S. Pat. No. 4,011,172 discloses articles designed to bleach fabrics in an automatic dryer comprising chlorine bleaching compounds dissolved in water or other suitable solvent thickened by the addition of particulate thickening agent, for example, silicate materials, water-swellable and water-soluble polyacrylamides and cellulose derivatives, and synthetic clays, the thickened bleaching compounds being contained in a perforated pouch made of plastic material until use, at which time the total contents of the pouch will be disseminated. The pouch comprises a flexible, embossed, water-insoluble plastic sheeting made by folding the embossed sheet into the pouch-like configuration and sealing, for example, heat-sealing, the edges, leaving an opening along one edge. After adding the bleaching composition to the pouch through the opening, the opening is then sealed. The resulting pouch is stretched immediately prior to use to cause pores or perforations along the embossing lines. Suitably embossed plastic sheets for preparing the pouch receptacle include sheets of, for example, polyethylene, polypropylene, and the like, and are available from Hercules as INSTANTNET and DELNET brand. When ruptured along the embossed pattern lines, such sheets form pores or perforations in the size range of 0.05 mm.–3 mm. Alternatively, water-insoluble plastic pouches having perforations in the size range of about 0.05 mm.–3 mm. can be used. Such pouches can be covered and sealed with plastic film which is removed at the time of use.

U.S. Pat. No. 4,170,565 discloses a substrate article for cleaning fabrics, particularly in an automatic washer, consisting essentially of an effective amount of a surface-active composition of about 5–95% by weight of a water-soluble surface-active agent contained between two layers of a water-insoluble, wet-strength substrate, at least one of said layers having an air permeability of at least about 10 ft.$^3$ of air per minute per ft.$^2$ of substrate. The perimeter of the two sheets are sealed together, such as by adhesive, sewing, or heat sealing. Preferred substrates include flexible water-insoluble, wet-strength paper, woven cloth, and non-woven cloth substrates, cellulose ester being mentioned among a list of synthetic fibers suitable for making non-woven cloths.

U.S. Pat. No. 4,289,815 discloses a pouch for the controlled release of active ingredients into an aqueous medium comprising liquid or solid active ingredients enclosed in a sealed envelop of cold-water insoluble polyvinyl alcohol. The object of the invention described in the patent is to provide pouches for delivery of active ingredients which provide a substantially uniform, controlled "zero-order" release of the active ingredients. This objective is achieved by utilizing cold-water insoluble, gas-impermeable polyvinyl alcohol as the polymeric film for preparing the pouches. The patent further discloses that a wide variety of liquid and solid active ingredients are applicable for use in the pouches, examples of which active ingredients include detergents, bleaches, chlorinating agents, pesticides, bactericides, dyes, drugs, and other chemicals. At column 3, lines 53 et seq., the patent teaches that "in order to establish practical release rates, it is required that the active ingredient exhibit a minimum water solubility" and that the water solubility can range from small water solubility to total water solubility. The patent also teaches that the applicable areas of use include introduction of active ingredients into toilet tanks, urinals, swimming pools, and water towers.

Isothiazolones are commonly provided in commerce in aqueous solutions, usually with inorganic, alkaline earth metal salts as a stabilizer to prevent reactions which render them inactive against microorganisms. Although solid alkaline earth metal salt complexes of isothiazolones are known (U.S. Pat. Nos. 4,150,026 and 4,241,214 mentioned above), these salt complexes suffer the disadvantage that they badly corrode processing equipment used to remove water in the course of producing the solid dry salt complex product, and the final solid salt complex product tends to be extremely dusty and thereby toxic to one during handling the product.

A typical, useful commercially available 3-isothiazolone product is a metal salt-stabilized aqueous solution of 5-chloro-2-methyl-3-isothiazolone and 2-methyl-3-isothiazolone (3:1) containing 14% active ingredient and Mg(NO$_3$)$_2$ plus MgCl$_2$ as stabilizers. Such commercial products suffer the disadvantages of being irritating to the skin when spilled during handling and evolving nontoxic gases which build up pressure in a sealed container provided for shipping and transportation.

It is an object of this invention to provide an improved microbiocidal, especially isothiazolone-containing, article for delivery of water-soluble, microbiocidally-effective compounds to aqueous systems wherein said article is characterized by possessing diminished, if any at all, tendency for a water-soluble microbiocidal, especially an isothiazolone, compound to accumulate on the external surface thereof, especially over a period of time which usually approximates a shipping and storage period.

Other biocides which may be employed include quaternary ammonium compounds such as N-alkyl dimethylbenzyl ammonium chloride and the like, dithiocarbamates such as 1,2-ethanediylbiscarbamodithioic acid disodium salt, sodium methyldithiocarbamate and the like, triazine such as hexahydro-1,3,5-tris-(2-hydroxyethyl)-S-triazine and the like and mercapto pyridines and zinc derivatives thereof such as sodium pyridinethione and the like.

This object, and other objects as will become apparent from the following description, is achieved by the present invention.

It now has been discovered that the use of a porous or perforated membrane, for example, a film or sheet of relatively hydrophobic film-forming material, wherein the pores or perforations are smaller than the particle size of a solid, particulate microbiocidal composition comprising an inert, finely-divided water-insoluble solid carrier material admixed with a water-soluble microbiocidal compound, especially a water-soluble isothiazolone compound in aqueous solution, prevents the particles of carrier material from flowing through the pores or perforations. The membrane can be employed in the production of microbiocidal articles useful for storing, handling, transporting, and delivering a microbiocidal compound to an aqueous system. The membrane is especially suitable for producing a microbiocidal article comprising the microbiocidal compound, especially isothiazolone, in solid form contained in a bag, or packet, of the membrane which is characterized by possessing diminished tendency, if any at all, for the microbiocidal compound, especially isothiazolone, to migrate through the membrane material and accumulate on the external surface of the packet.

This invention is, then, also a method for safening the handling of microbiocidal compounds, especially isothiazolones, which comprises employing a sealed, porous membrane, especially one having a film thickness of from about 0.5 mil to about 10 mils and having a pore size sufficiently smaller than the particle size of the particulate, solid microbiocidal composition defined hereafter, especially those having a pore diameter equal to or less than 6 mil and more especially those having a pore diameter of about 5 mil, containing sealed therein a particulate, solid microbiocidal composition comprising (i) an aqueous solution containing about 0.1 to 70 weight %, based on total weight of said composition, of at least one water-soluble microbiocide, especially one whose water solubility is greater than 1000 ppm, blended with and absorbed in (ii) about 99.9 to 30 weight %, based on total weight of said composition, of an inert, finely-divided water-insoluble solid carrier material, the improvement wherein the porous membrane is selected from hydrophobic, film-forming materials having a solubility parameter less than about 12.5.

Suitable hydrophobic, film-forming materials are polyesters, polyfluoroolefins, polyamides (Nylons), polyvinyl chloride, polyethylene, polypropylene, spunbonded polyethylene, spunbonded polypropylene, polyethylene terephthalate, or polycarbonate.

In another aspect, this invention is an article useful for storing, handling, transporting, and providing a water-soluble microbiocidal compound in a method for controlling isothiazole living microorganisms in an aqueous system comprising:

(a) a porous membrane produced from a porous or perforated film or sheet of a film-forming material having a film thickness of from 0.5 mil to about 10 mils and having a pore size sufficiently smaller than the particle size of the particulate, solid microbiocidal isothiazolone composition defined hereafter containing sealed therein a particulate, solid microbiocidal isothiazolone composition comprising (i) an aqueous solution containing about 0.1 to 70 weight %, based on total weight of said composition, of at least one water-soluble microbiocidally-effective isothiazolone, whose water solubility is greater than 1000 ppm, blended with (ii) about 99.9 to 30 weight %, based on total weight of said composition, of an inert, finely-divided water-insoluble solid carrier material, the improvement wherein the film-forming material is selected from hydrophobic film-forming material having a water solubility parameter less than about 12.5.

In yet another aspect, the invention is a method for controlling living microorganisms in an aqueous system which comprises introducing into the aqueous system the improved article of this invention containing sufficient particulate, solid microbiocidal isothiazolone composition to provide in the aqueous system a microbiocidally effective amount of said isothiazolone.

Microbiocides or biocides, especially those isothiazolones which have high water solubility and which have been found to be especially useful, preferably are absorbed into the inert, finely-divided, water-insoluble solid carrier material from aqueous solutions, in which form they, the isothiazolones, are ordinarily obtained from conventional production processes. When it is desirable to package the particulate, solid microbiocidal isothiazolone composition of the aqueous solution of the isothiazolone absorbed into the solid carrier material, the film-forming membrane material used to envelope the composition to form the article or packet must possess the characteristic that the water of absorption containing dissolved isothiazolone will not migrate from the interior of the article through the membrane material to the external surface of the article so as to result in an accumulation of the isothiazolone on the external surface of the article. A hydrophobic material is best suited for not permitting aqueous solutions containing isothiazolones which may leach-out from the composition to migrate from the interior of the article to the external surface. However, continuous films of hydrophobic materials used as the membrane for the article will permit only small amounts of aqueous solutions containing isothiazolones to migrate from the interior to the exterior surface of the article and permit only small amounts of external water to migrate from the external environment of use of the article into the interior of the article. Thus, such continuous films of hydrophobic material permit the release of only small amounts of the microbiocidal isothiazolones from the composition of the external aqueous system which constitutes the environment of use. Although continuous films of hydrophobic material are useful to produce articles which will provide protracted release of small amounts of isothiazolones to effect low concentrations thereof in the environment of use, such films are not suitable to effect higher concentrations of isothiazolones in the environment of use.

This problem is overcome by the use, for the article membrane, of a porous or perforated film or sheet produced from hydrophobic film-forming material. The pores or perforations may be effected by punching holes in the film or sheet, or by a method of manufacture of the film or sheet which will impart pores or perforations to the film or sheet, for example, weaving or spunbonding manufacturing methods. The only limitation concerning the pore size is that it be sufficiently smaller than the particle size of the particulate, solid microbiocidal isothiazolone composition so as to not permit the composition to pass from the interior of the article through the pores to the external environment of use. Pore sizes in the range of from about 4 to about 7 mils are generally preferred.

The surprising characteristic property of the article produced is that when the article is used in an aqueous system, water freely migrates through the membrane pores into the interior of the article and dissolves the water-soluble microbiocides from the composition and migrates as an aqueous microbiocide solution back into the aqueous system. This converts the initial aqueous system into a solution containing microbiocidally-effective amounts of biocides released from the article. This same article, when dry prior to use, does not permit migration of the absorbed aqueous solution of the microbiocide from the interior of the article to accumulate on the external surface of the article even over a period of time which approximates shipping or transporting and storage time under normal room conditions of relative humidity and temperature, notwithstanding the presence of the pores in the enveloping membrane or packet material.

It will be apparent to those having ordinary skill in the pertinent art that the porous membrane of hydrophobic material is also useful to produce articles according to this invention wherein the particulate, solid microbiocidal isothiazolone composition is produced from solutions of the water-soluble isothiazolone component dissolved in water or in a volatile organic solvent absorbed onto the carrier material followed by removal, by conventional means of evaporation, of the water or the volatile organic solvent before the composition is enveloped or sealed in the porous membrane or packet material. In this embodiment, this invention is also advantageous in that the use of the porous film of hydrophobic material prohibits the accumulation of the isothiazolone component in aqueous solution on the external surface of the article wherein the water provided by the storage environment, that is, humid air, is permitted to migrate from the external storage environment through the porous membrane into the interior of the article, but no resulting aqueous isothiazolone solution formed in the interior of the article is permitted to migrate back through the membrane to the external surface of the article.

Thus, the article according to this invention provides the further improvement that the article affords a still safer form of water-soluble biocides, especially isothiazolones, useful in aqueous systems, which form is characterized by more reduced risk of contact of the biocide, especially isothiazolones, in aqueous solution with the skin.

Desirable ranges of hydrophobicity of film-forming material useful for producing the article membrane are set forth below:

| Desirability | Article Membrane Material | Solubility Parameter |
|---|---|---|
| Poor | eg, polyvinyl alcohol, cellulose | >12.5<br>12.6<br>15.6 |
| Preferred | eg, polyamide, polyvinyl chloride | 10–12.5<br>12<br>12.2 |
| More Preferred | eg, polyethylene terephthalate, polycarbonate | 8–10<br>9.5<br>9.5 |
| Most Preferred | eg, polyethylene, polypropylene | <8<br>7.8<br>7.8 |

Preferably, in the particulate, solid microbiocidal isothiazolone composition used according to the invention, the water-soluble microbiocidally-effective isothiazolone (i), having a water solubility of greater than 1000 ppm, is respresented by the formula

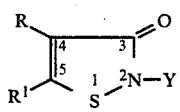

wherein

Y is an unsubstituted or substituted $C_1$–$C_{18}$ alkyl group, an unsubstituted or substituted $C_2$–$C_{18}$ alkenyl or alkynyl group, an unsubstituted or substituted $C_3$–$C_{12}$ cycloalkyl group, an unsubstituted or substituted aralkyl group of 6–10 carbon atoms, or an unsubstituted or substituted aryl group of 6–10 carbon atoms;

R is hydrogen, halogen or a $C_1$–$C_4$ alklyl group;

R' is hydrogen, halogen or a $C_1$–$C_4$ alkyl group, or R and R' can be taken together with the C=C bond of the isothiazolone ring to form a benzene ring;

or at least one of said isothiazolones stabilized with at least one metal salt used in an amount of about 1–60 weight %, based on weight of isothiazolone and metal salt, said metal salt being represented by the formula:

$$(MX_n)$$

wherein

M is a cation of a metal selected from sodium, potassium, calcium, magnesium, copper, iron, zinc, barium, manganese, silver, cobalt and nickel;

X is an anion selected from chloride, bromide, iodide, sulfate, nitrate, nitrite, acetate, chlorate, perchlorate, bisulfate, bicarbonate, oxalate, maleate, p-toluene-sulfonate, carbonate, and phosphate; and n is an integer for which the anion X satisfies the valence of the cation M;

and, said solid carrier material (ii) comprises an inert, finely-divided water-insoluble solid material selected from silicaceous diatomaceous earth, high water absorption capacity calcium silicate granular material, silicas, charcoal, clays, vermiculite, corn cobs, wood (sawdust), polymeric matrices, such as ion exchange resin beads, and the like.

It is to be understood that, as the number of carbon atoms in the substituent group "Y" increases, and as halogens are substituted on the isothiazolone ring, water-solubility decreases.

By a "substituted alkyl group" is meant an alkyl group having one or more of its hydrogens replaced by another substituent group. Examples of the substituted alkyl groups which characterize the isothiazolones used in this invention include hydroxyalkyl, haloalkyl, cyanoalkyl, alkylamino, dialkylamino, arylaminoalkyl, carboxyalkyl, carbalkoxyalkyl, alkoxyalkyl, aryloxyalkyl, alkylthioalkyl, arylthioalkyl, haloalkoxyalkyl, cycloamanoalkyl such as morpholinylalkyl and piperidinylalkyl and pyrrolodinylalkyl and the like, carbamoxyalkyl, alkenyl, haloalkenyl, alkynyl, haloalkynyl, isothiazolonylalkyl, and the like.

By a "substituted aralkyl group" is meant an aralkyl group having one or more of phe hydrogens on either the aryl ring or the alkyl chain replaced by another substituent group. Examples of the substituted aralkyl group which characterize the isothiazolones used in this invention include halo, lower alkyl, lower alkoxy, and the like.

By a "substituted aryl group" and "substituted benzene ring" is meant an aryl group and benzene ring, respectively, such as phenyl, naphthyl, or pyridyl groups, having one or more of the hydrogens on the aryl ring replaced by another substituent group. Examples of such substituent groups include halo, nitro, lower alkyl, lower alkoxy, lower alkyl- and acylamino, lower carbalkoxy, sulfonyl, and the like.

By the expression "water-soluble" as applied to the isothiazolones used in this invention is meant an isothiazolone or combination of isothiazolones characterized by having a water solubility greater than 1000 ppm (0.1%). Especially preferably, the isothiazolone or combination thereof is characterized by having a water solubility greater than 50,000 ppm. An example of a suitable highly water-soluble combination of isothiazolones is the commercially available 3-isothiazolone product, 5-chloro-2-methyl-3-isothiazolone and 2-methyl-3-isothiazolone in a weight ratio of 3:1 with 15 weight % Mg (NO$_3$)$_2$ and 9 weight % of Mg Cl$_2$, whose water solubility is about 150,000 ppm. The isothiazolone may have a water solubility even approaching infinite solubility.

By the expression "microbiocidal compound" is meant those compounds effective to control those microorganisms especially of the group of bacteria, fungi (including molds and yeasts), and algae. In the method of the invention for controlling living microorganisms, by the expression "microorganisms" is meant bacteria, fungi (including molds and yeasts), and algae.

When used alone, the expression "isothiazolone(s)" is meant to include the "free" isothiazolone(s) and the metal salt complexes of the free isothiazolone(s).

More preferably in the methods and article of the invention, the particulate, solid, microbiocidal isothiazolone composition comprises (i) about 1 to 35 weight %, based on total weight of said composition, of said water-soluble isothiazolone wherein Y is an unsubstituted or substituted $C_1$–$C_{18}$ alkyl group or $C_3$–$C_{12}$ cycloalkyl group;

R is hydrogen or halogen;

R' is hydrogen or halogen; or

R and R' are taken together with the C=C bond of the isothiazolone ring to form a benzene ring;

or said isothiazolone stabilized with said metal salt; and (ii) about 99 to 65 weight%, based on total weight of said composition, of a solid carrier material selected from silicaceous diatomaceous earth, high water absorption capacity calcium silicate granular material, silicas and clays.

Most preferably in the methods and article of the invention, the particulate, solid, microbiocidal isothiazolone composition comprises (i) about 2 to 25 weight %, based on total weight of said composition, of said water-soluble isothiazolone wherein Y is methyl, R is hydrogen and R' is chlorine; or of a mixture of said isothiazolones in aqueous solution wherein Y is methyl, R is hydrogen and R' is chlorine and Y is methyl, R is hydrogen and R' is hydrogen; or said isothiazolone(s) stabilized with said metal salt wherein said metal salt is $Mg(NO_3)_2$ or a mixture of $Mg(NO_3)_2$ and $MgCl_2$; and (ii) about 98 to 75 weight %, based on total weight of said composition, of silicaceous diatomaceous earth.

By way of example, there may be used in combination with the above-defined 3-isothiazolone commercial product, an isothiazolone having a water-solubility of about 500 ppm wherein Y is n-octyl or t-octyl and R and R' are both hydrogen, providing, of course, that the water solubility of the combination is greater than 1000 ppm.

The preparation and properties of representative isothiazolones are described in U.S. Pat. Nos. 3,517,022; 3,761,488; and 3,065,123. U.S. Pat. No. 3,849,430 further discloses a process for the preparation of representative isothiazolones. U.S. Pat. Nos. 3,870,795 and 4,067,878 describe metal salt stabilized solutions of 3-isothiazolones which are useful according to this invention. Additional isothiazolones which are useful according to the invention are those disclosed in U.S. Pat. No. 4,310,590.

Preferably, the finely-divided, water-insoluble solid carrier material is selected from silicaceous diatomaceous earth, high water absorption capacity calcium silicate material, silicas, clays, and polymeric matrices.

Suitable silicaceous diatomaceous earth material is described in the Johns-Manville Corporation Technical Bulletin FF-160A, 10-80 concerning Celite ® Diatomite Filter Aids and Natural, Calcined, and Flux-Calcined Grades thereof. Suitable high water absorption capacity calcium silicate material is commercially available under the trademark "Micro-Cel" from the Johns-Manville Corporation. Typical as polymeric matrices useful as carrier material are ion exchange adsorbents, such as, for example, Amberlite ® XAD-4 (a styrene/divinylbenzene polymeric ion exchange adsorbent); Amberlite ® XAD-7 and Amberlite XAD-8 (acrylic ion exchange adsorbents); Amberlite ® 200 (a sulfonated styrene/divinylbenzene ion exchange adsorbent); Amberlite ® IRA-900 (a styrene/divinylbenzene strong base ion exchange adsorbent), and Amberlite ® IRC-50 (a weak acid ion exchange adsorbent).

Especially preferred is a diatomaceous earth material commercially available as Celite ® 545 (Johns-Manville Corporation).

Of course, conventional adjuvants and additives used in microbiocidal compositions and formulations may be incorporated into the solid microbiocidal composition by first dissolving them in the aqueous or inert organic solvent solution of the isothiazolone(s) and then blending the solution with the solid carrier material. One useful additive for use in the solid microbiocidal composition according to the invention is a dye which would impart a readily visible color to the solid composition. Thus, whenever, as a result of the accidental rupture of the article according to the invention, any solid microbiocidal composition would accidently be spilled onto the skin during handling, the spilled composition could readily be observed and removed before the toxicant could leach out of the solid and cause skin burns. This is in contrast to the case involving accidental spillage of the aqueous microbiocidal solution of the isothiazolone when handling in association with an aqueous system, in which case it would be difficult to distinguish between harmless aqueous system and toxic isothiazolone concentrate. Other useful adjuvants and additives include chelating agents, surfactants, dispersants, buffers, and the like.

Alternatively, other conventional adjuvants and additives used with the isothiazolones which are used according to this invention may be combined with the microbiocidal composition in the sealed membrane independent of incorporation into the microbiocidal composition.

The article of the invention may be used advantageously in metal-working fluids, swimming pools, water towers such as water cooling towers, toilet bowl water, washing machine water, and the like.

For use in metal-working fluids, swimming pools, water towers, such as water cooling towers, toilet bowl water, washing machine water, and the like, the article of the invention can conveniently be removed from its shipping container, placed into the aqueous system to be treated, and, when the microbiocidal compound has completely leached-out of the article, the sealed membrane containing the solid carrier material can be safely removed by conventional techniques, for example, by hand, using tongs to dip the sealed membrane from the aqueous system.

The following examples are illustrative of the invention and are not intended to limit it in any way. All parts and percentages are by weight unless otherwise indicated and all temperatures are in degrees Centigrade unless otherwise indicated.

EXAMPLE 1

To 75 g. of Celite ® 545 in a glass bottle was added 75 g. of 5-chloro-2-methyl-3-isothiazolone blended with 2-methyl-3-isothiazolone in a weight ratio of 3:1 (approx.) with 15 weight % $Mg(NO_3)_2$ and 9 weight % of $MgCl_2$ in aqueous solution containing 14% active ingredient. The mixture was then stirred by hand with a spatula until it appeared to be uniformly mixed and free-flowing. No drying by heating was required or desired. The resulting solid product contained one-half of the initial amount of active ingredient ("AI") per unit weight of product, that is, the solid composition contained 7 weight % of active ingredient. The resulting solid microbiocidal composition was stored in a sealed bottle for several days at room temperature. Thereafter, when the stopper was removed, there was observed no gas emission due to pressure build-up.

1.6 g. of the resulting solid microbiocidal composition was added to 1000 ml. of water to give 1001.6 g. total weight of water and solid microbiocidal composition. Analysis of the supernatant water by ultraviolet spectroscopy indicated that all of the microbiocide 886 was released into the water within 5 minutes.

EXAMPLE 2

A solid microbiocidal composition containing 20 weight % of active ingredient was prepared by dissolving 2.66 g. of crystalline 5-chloro-2-methyl-3-isothiazolone in 15 ml. of methanol. To this solution there was added 0.6 g of $Mg(NO_3)_2.6H_2O$. The resulting solution was added to 10 g. of Celite 545 in a 4 fl. oz. bottle and the mixture was stirred by hand using a spatula until it appeared to be uniformly mixed and free-flowing. Methanol was removed by air-drying (or by heating the mixture under reduced pressure), and a uniform, free-flowing particulate solid was obtained. The solid was stored in a sealed bottle for several days at room temperature and thereafter, when the stopper was removed, there was observed no gas emission due to pressure build-up resulting from gas evolution from the solid composition. Upon adding the solid composition to water, all of the isothiazolone was released within 10 minutes.

EXAMPLE 3

This example illustrates the property of the solid microbiocidal composition whereby the solid composition tends not to evolve gasses to the extent that the known aqueous solutions of 3-isothiazolones evolve gasses even after heat treatment to eliminate volatile components.

The solid compositions were prepared as follows:

Water was partially removed from Kathon ® 886 aqueous concentrate under reduced pressure (65° C./40 mm Hg), and solid carrier material (Celite ® 545, available from Johns-Manville Corporation; Attaclay ® X-250, available from the Minerals and Chemicals Corporation of America, Attapulgus Clay Products; HiSil T-600, available from Pittsburgh Plate and Glass Company; or mixtures thereof) was added to the residue to obtain a flowable solid composition.

The table below describes the formulation and properties of representative compositions.

SOLID FORMULATIONS FROM A 3:1 (approx.) WEIGHT MIXTURE OF 5-CHLORO-2-METHYL-3-ISOTHIOAZOLONE and 2-METHYL-3-ISOTHIAZOLONE, 14% ACTIVE INGREDIENT IN AQUEOUS SOLUTION, WITH 15% Mg(NO$_3$)$_2$ and 7% MgCl$_2$ LIQUID CONCENTRATE

| | | Components of the Formulations | | | | | | Pressure (psig) 25° C. After 15 Hrs. @ 93° C. | % Active Ingred. (by GLC) | |
| --- | --- | --- | --- | --- | --- | --- | --- | --- | --- | --- |
| Form. Number | % AI | % Mg(NO$_3$)$_2$ 6H$_2$O | % MgCl$_2$ 6H$_2$O | % "Free" H$_2$O | % Celite 545[3] | % Attaclay ®[4] X-250 | % HiSil ®[5] T-600 | | Before Gassing Test | After Gassing Test |
| 3A | 14.1 | 25.9 | 19.2 | 1.3 | 29.3 | — | 10.2 | 2.6 | 13.6 | 11.5 |
| 3B | 14.07 | 25.9 | 19.2 | 0.1 | — | 29.9 | 10.8 | 1.4 | 11.4 | 10.7 |
| Control | 14.0 | 15.9 | 19.2 | 40.9 | — | — | — | 12–13 | 14 | 13.8 |

[3]Celite 545 available from Johns-Manville Corporation.
[4]Attaclay X-250 available from the Attapulgus Clay Company.
[5]HiSil T-600 available from the Pittsburgh Plate and Glass Company.

EXAMPLE 4

There was sealed in bags, or packets or pouches, of the representative porous films, each packet having 20 in.$^2$ of surface area (10 in.$^2$ on each side), 28.6 gm. of the solid isothiazolone composition produced according to Example 1. The packets are heat-aged three days at 50° C., and one 10 in.$^2$ surface of each packet is wiped with a water-dampened tissue to remove any AI residing on the packet's surface. The AI is then extracted from the tissue by 100 ml. of dionized water, and the amount of AI present in the water is determined by ultraviolet spectroscopy by comparing the absorbance at 273 nm with that of a standard solution. The results are as follows:

| | |
| --- | --- |
| TYVEK 1621* | 0.001 mg./in.$^2$ |
| TYVEK 1622E* | 0.004 mg./in.$^2$ |
| Cellophane** | 0.105 mg./in.$^2$ |

*Spunbonded and perforated polyethylene from Dupont.
**Clear film (unperforated) from Olin, #126 PUT-76.

What is claimed is:

1. In a method for safening the use of microbiocidal compositions which comprises placing said compositions in a sealed porous membrane article prepared from a hydrophobic material having a thickness of from about 0.5 mil to about 10 mils and having a pore size smaller than the effective particle size of the solid microbiocidal composition contained sealed therein; the particulate solid microbiocidal composition comprising:
   (i) an aqueous solution containing about 0.1 to 70 weight %, based on total weight of said composition, of at least one water-soluble microbiocidal compound blended with and absorbed into;
   (ii) about 99.9 to 30 weight %, based on total weight of said composition, of an inert, finely-divided water-insoluble solid carrier material:
the improvement wherein the porous membrane is selected from hydrophobic film-forming materials having a solubility parameter less than 12.5.

2. The method according to claim 1 wherein said membrane is produced from polyester, polyfluoroolefins, polyamides, polyvinyl chloride, polyethylene, polypropylene, spunbonded polyethylene, spunbonded polypropylene, polyethylene terephthalate, or polycarbonate.

3. The method according to claim 2 wherein said membrane is produced from spunbonded polyethylene or spunbonded polypropylene.

4. The method according to claim 2 wherein said microbiocide is selected from at least one water-soluble microbiocidally-effective isothiazolone, having a water solubility of greater than 1000 ppm, represented by the formula:

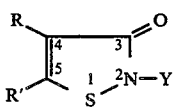

wherein
Y is an unsubstituted or substituted C$_1$–C$_{18}$ alkyl group, an unsubstituted or substituted C$_2$–C$_{18}$ alkenyl or alkynyl group, an unsubstituted or substituted C$_3$–C$_{12}$ cycloalkyl group, an unsubstituted or substituted aralkyl group of 6–10 carbon atoms, or an unsubstituted or substituted aryl group of 6–10 carbon atoms;

R is hydrogen, halogen or a $C_1$–$C_4$ alkyl group,

R' is hydrogen, halogen or a $C_1$–$C_4$ alkyl group; or

R and R' are taken together with the C=C bond of the isothiazolone ring to form a substituted or unsubstituted benzene ring;

or at least one of said isothiazolones stabilized with at least one metal salt used in an amount of about 1–60 weight %, based on weight of 3-isothiazolone and metal salt, said metal salt being represented by the formula:

$$(MX_n)$$

wherein

M is a cation of a metal selected from sodium, potassium, calcium, magnesium, copper, iron, zinc, barium, manganese, silver, cobalt and nickel;

X is an anion selected from chloride, bromide, iodide, sulfate, nitrate, nitrite, acetate, chlorate, perchlorate, bisulfate, bicarbonate, oxalate, maleate, p-toluene-sulfonate, carbonate, and phosphate; and n is an integer for which the anion X satisfies the valence of the cation M.

5. The method of claim 2 wherein the solid carrier material is selected from siliceous diatomaceous earth, high water absorption capacity calcium silicate granular material, silicas, clays, charcoal, vermiculite, corn cobs, wood and polymeric matrices.

6. The method according to claim 5 wherein said article comprises from about 1 to 35 weight %, based on total weight of composition, of isothiazolone wherein Y is an unsubstituted or substituted $C_1$–$C_{18}$ alkyl group or $C_3$–$C_{12}$ cycloalkyl group; R is hydrogen or halogen;

R' is hydrogen or halogen; or R and R' are taken together with the C=C bond of the 3-isothiazolone ring to form a substituted or unsubstituted benzene ring; an isothiazolone stabilized with a metal salt or combinations thereof; and from about 99 to 65 weight %, based on total weight of composition, of a solid carrier material selected from siliceous diatomaceous earth, high water absorption capacity calcium silicate granular material, silicas, and clays.

7. The method according to claim 6 wherein said article comprises from about 2 to 25 weight %, based on total weight of composition, of an isothiazolone wherein Y is methyl, R is hydrogen, and R' is chlorine, an isothiazolone stabilized with said metal salt wherein said metal salt is $Mg(NO_3)_2$ or a mixture of $Mg(NO_3)_2$ and $MgCl_2$; or combinations thereof, and from about 98 to 75 weight %, based on total weight of said isothiazolone, of siliceous diatomaceous earth.

8. The method according to claim 7 wherein the article comprises, in combination with said water-soluble isothiazolone, an isothiazolone having a water solubility of about 500 ppm wherein Y is n-octyl or t-octyl and R and R' are each hydrogen, or an aqueous solution of said isothiazolones stabilized with $Mg(NO_3)_2$ or a mixture of $Mg(NO_3)_2$ and $MgCl_2$, the isothiazolone comprising from about 2 to 25 weight %, based on total weight of the composition; and from about 98 to 75 weight %, based on total weight of said composition, of siliceous diatomaceous earth and the pore size of the membrane is equal to or less than 6 mil.

9. The method according to claim 8 wherein the article comprises from about 2 to 25 weight %, based on total weight of said article, of a mixture of an isothiazolone in an aqueous solution wherein Y is methyl, R is hydrogen and R' is chlorine and Y is methyl, R is hydrogen and R' is hydrogen, or an aqueous solution of said mixture of isothiazolones stabilized with $Mg(NO_3)_2$ or a mixture of $Mg(NO_3)_2$ and $MgCl_2$; and from about 98 to about 75 weight %, based on total weight of said article, of siliceous diatomaceous earth and the pore size of the membrane is about 5 mils.

* * * * *